US011122250B2

(12) United States Patent
Ito

(10) Patent No.: US 11,122,250 B2
(45) Date of Patent: Sep. 14, 2021

(54) THREE-DIMENSIONAL IMAGE PROJECTION APPARATUS, THREE-DIMENSIONAL IMAGE PROJECTION METHOD, AND THREE-DIMENSIONAL IMAGE PROJECTION CONTROL PROGRAM

(71) Applicant: FUJIFILM Corporation, Tokyo (JP)

(72) Inventor: Hirotaka Ito, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/292,370

(22) Filed: Mar. 5, 2019

(65) Prior Publication Data

US 2019/0199996 A1 Jun. 27, 2019

Related U.S. Application Data

(63) Continuation of application No. PCT/JP2017/024744, filed on Jul. 6, 2017.

(30) Foreign Application Priority Data

Sep. 28, 2016 (JP) .............................. JP2016-189795

(51) Int. Cl.
*H04N 13/167* (2018.01)
*H04N 13/363* (2018.01)
*H04N 9/31* (2006.01)
*G06T 7/70* (2017.01)
*A61B 90/00* (2016.01)
(Continued)

(52) U.S. Cl.
CPC ........... *H04N 13/167* (2018.05); *A61B 5/055* (2013.01); *A61B 6/03* (2013.01); *A61B 90/361* (2016.02);
(Continued)

(58) Field of Classification Search
CPC .. H04N 13/167; H04N 13/363; H04N 9/3185; A61B 90/361; A61B 90/37;
(Continued)

(56) References Cited

U.S. PATENT DOCUMENTS 6,175,610 B1 1/2001 Peter
8,896,688 B2 * 11/2014 Blanton ................... G06K 9/00
345/156
(Continued)

FOREIGN PATENT DOCUMENTS

JP H05-161635 A 6/1993
JP H09-117446 A 5/1997
(Continued)

OTHER PUBLICATIONS

International Search Report issued in PCT/JP2017/024744; dated Oct. 3, 2017.
(Continued)

*Primary Examiner* — Hesham K Abouzahra
(74) *Attorney, Agent, or Firm* — Studebaker & Brackett PC

(57) ABSTRACT

A three-dimensional image projection apparatus includes: a screen recognition unit 12 that recognizes a position of a screen which is randomly provided and a posture of the screen in a three-dimensional space; a projection unit 30 that projects a projection image of a three-dimensional image of a subject on the screen on the basis of the position of the screen recognized by the screen recognition unit 12; and a three-dimensional image processing unit 11 that changes parameters of three-dimensional image processing performed for the three-dimensional image, on the basis of the posture of the screen in the three-dimensional space which is recognized by the screen recognition unit 12.

22 Claims, 7 Drawing Sheets

(51) Int. Cl.
*G06K 9/00* (2006.01)
*A61B 6/03* (2006.01)
*G03B 21/14* (2006.01)
*A61B 5/055* (2006.01)

(52) U.S. Cl.
CPC .............. *A61B 90/37* (2016.02); *A61B 90/39* (2016.02); *G03B 21/14* (2013.01); *G06K 9/00201* (2013.01); *G06T 7/70* (2017.01); *H04N 9/3185* (2013.01); *H04N 13/363* (2018.05); *A61B 2090/364* (2016.02); *A61B 2090/372* (2016.02); *A61B 2090/3983* (2016.02); *G06T 2207/30004* (2013.01); *G06T 2207/30204* (2013.01)

(58) Field of Classification Search
CPC ........... A61B 90/39; A61B 5/055; A61B 6/03; G06T 7/70; G03B 21/14; G06K 9/00201
See application file for complete search history.

(56) References Cited

U.S. PATENT DOCUMENTS

| | | | |
|---|---|---|---|
| 9,451,245 B1 * | 9/2016 | Darling | G06T 7/74 |
| 2002/0071101 A1 * | 6/2002 | Horbaschek | A61B 6/00 353/28 |
| 2008/0033410 A1 * | 2/2008 | Rastegar | A61B 18/20 606/9 |
| 2008/0198968 A1 | 8/2008 | Takekoshi et al. | |
| 2017/0094236 A1 * | 3/2017 | Kiriyama | H04N 5/332 |

FOREIGN PATENT DOCUMENTS

| | | |
|---|---|---|
| JP | H11-313801 A | 11/1999 |
| JP | 2000-278714 A | 10/2000 |
| JP | 2002-62842 A | 2/2002 |
| JP | 2002-112993 A | 4/2002 |
| JP | 2007-264334 A | 10/2007 |
| JP | 2008-194374 A | 8/2008 |
| JP | 2008-237369 A | 10/2008 |
| JP | 2008-242087 A | 10/2008 |

OTHER PUBLICATIONS

International Preliminary Report on Patentability and Written Opinion issued in PCT/JP2017/024744; dated Apr. 2, 2019.
An Office Action; "Notice of Reasons for Refusal," issued by the Japanese Patent Office dated Aug. 6, 2019, which corresponds to Japanese Patent Application No. 2018-541926 and is related to U.S. Appl. No. 16/292,370; with English Translation.

* cited by examiner

THREE-DIMENSIONAL IMAGE PROJECTION APPARATUS, THREE-DIMENSIONAL IMAGE PROJECTION METHOD, AND THREE-DIMENSIONAL IMAGE PROJECTION CONTROL PROGRAM

CROSS REFERENCE TO RELATED APPLICATIONS

This application is a Continuation of PCT International Application No. PCT/JP2017/024744 filed on Jul. 6, 2017, which claims priority under 35 U.S.C. § 119(a) to Patent Application No. 2016-189795 filed in Japan on Sep. 28, 2016, all of which are hereby expressly incorporated by reference into the present application.

BACKGROUND OF THE INVENTION

1. Field of the Invention

The present invention relates to a three-dimensional image projection apparatus, a three-dimensional image projection method, and a non-transitory computer recording medium storing a three-dimensional image projection control program that project a projection image of a three-dimensional image of a subject which has been captured in advance on a screen.

2. Description of the Related Art

In recent years, an organ model formed by a three-dimensional image of a patient to be operated on has been actively used at the time of a preoperative plan. Further, it is desired to refer to the organ model of the patient created at the time of the preoperative plan even during an operation. In some cases, a method for displaying the organ model of the patient on a monitor in an operating room is used. However, in this case, an operator needs more work to shift his or her gaze between the affected part of the patient and the monitor.

SUMMARY OF THE INVENTION

Therefore, a method has been proposed which directly superimposes an organ model created from a three-dimensional image of the patient to be operated on before an operation on the organ of the patient using a projector and refers to the organ model.

However, it may be difficult to correctly check a projection image in a case in which the projection image of the organ model is directly projected on an operative field that has a complicated shape and includes various colors.

For this reason, for example, a method is considered in which a screen is provided on a patient who lies on a bed and a projection image is projected on the screen, as disclosed in JP1997-117446A (JP-H09-117446A).

However, in the configuration in which the projection image is projected on the screen as described above, for example, in a case in which a user wants to change the posture of a projection image of a three-dimensional image displayed on the screen and to observe the projection image, the user needs to input a command to change parameters in a three-dimensional image processing apparatus in order to perform three-dimensional image processing for changing posture for the three-dimensional image. Manually setting and inputting the parameter change command to the apparatus causes sanitary problems not only for the surgeon but also for other assistants. That is, the surgeon or the assistant is likely to be contaminated by touching the three-dimensional image processing apparatus.

An operation of inputting a command to change the settings of parameters to the three-dimensional image processing apparatus for a limited time, such as during an operation, is complicated and it takes a lot of time to perform the operation.

In addition, JP2008-242087A and JP2007-264334A disclose content related to a projector that projects an image on a screen and do not disclose any technique that changes parameters of three-dimensional image processing in a case in which a projection image of a three-dimensional image is projected on the screen as described above.

The invention has been made in view of the above-mentioned problems and an object of the invention is to provide a three-dimensional image projection apparatus, a three-dimensional image projection method, and a non-transitory computer recording medium storing a three-dimensional image projection control program that can easily change parameters of three-dimensional image processing, without any sanitary problems, in a case in which a projection image of a three-dimensional image is projected on a screen.

According to the invention, there is provided a three-dimensional image projection apparatus comprising: a screen recognition unit that recognizes a position of a screen and a posture of the screen in a three-dimensional space; a projection unit that projects a projection image of a three-dimensional image of a subject on the screen on the basis of the position of the screen recognized by the screen recognition unit; and a three-dimensional image processing unit that changes parameters of three-dimensional image processing performed for the three-dimensional image, on the basis of a change in the posture of the screen in the three-dimensional space, which is recognized by the screen recognition unit, or a change in the projection image of the three-dimensional image projected on the screen.

In the three-dimensional image projection apparatus according to the invention, the three-dimensional image processing unit may change the parameters of the three-dimensional image processing on the basis of the posture of the screen in the three-dimensional space to change the posture of the projection image of the three-dimensional image.

In the three-dimensional image projection apparatus according to the invention, the three-dimensional image processing unit may change the parameters of the three-dimensional image processing on the basis of the posture of the screen in the three-dimensional space to perform a rotation process for the three-dimensional image.

In the three-dimensional image projection apparatus according to the invention, the rotation process may be a rotation process using, as a rotation axis, a straight line that extends in a plane of a coordinate system of the three-dimensional image which corresponds to a projection surface of the screen.

In the three-dimensional image projection apparatus according to the invention, in a case in which the screen is moved, the screen recognition unit may recognize a position of the screen after the movement and the projection unit may project the projection image on the screen after the movement.

In the three-dimensional image projection apparatus according to the invention, the screen recognition unit may detect a marker provided on the screen to recognize the position of the screen and the posture of the screen in the three-dimensional space.

In the three-dimensional image projection apparatus according to the invention, the screen recognition unit may detect the screen to recognize the position of the screen and the posture of the screen in the three-dimensional space.

In the three-dimensional image projection apparatus according to the invention, the screen recognition unit may recognize a change in the projection image of the three-dimensional image projected on the screen and the three-dimensional image processing unit may change the parameters of the three-dimensional image processing in a case in which the screen recognition unit recognizes the change in the projection image of the three-dimensional image.

In the three-dimensional image projection apparatus according to the invention, the projection unit may project a projection image of an operation marker on the screen. The screen recognition unit may recognize a change in the projection image of the operation marker. The three-dimensional image processing unit may change the parameters of the three-dimensional image processing in a case in which the screen recognition unit recognizes the change in the projection image of the operation marker.

In the three-dimensional image projection apparatus according to the invention, the three-dimensional image processing unit may change the parameters of the three-dimensional image processing to change transparency of the three-dimensional image.

In the three-dimensional image projection apparatus according to the invention, the projection unit may project an index indicating a projection range of the projection unit.

The three-dimensional image projection apparatus according to the invention may further comprise an imaging unit that captures an image of the screen. The screen recognition unit may recognize the position of the screen and the posture of the screen in the three-dimensional space on the basis of the image captured by the imaging unit.

In the three-dimensional image projection apparatus according to the invention, preferably, an arrangement relationship between the projection unit and the imaging unit may be fixed in advance.

In the three-dimensional image projection apparatus according to the invention, preferably, the projection unit and the imaging unit may have an arrangement relationship in which optical axes of the projection unit and the imaging unit are aligned with each other and angles of view of the projection unit and the imaging unit are matched with each other.

In the three-dimensional image projection apparatus according to the invention, the imaging unit and the projection unit may be configured such that a position or a posture of the imaging unit and the projection unit is changeable.

In the three-dimensional image projection apparatus according to the invention, the projection unit may project the projection images on a plurality of the screens which are provided in one projection range.

In the three-dimensional image projection apparatus according to the invention, the projection unit may project different projection images on the plurality of screens.

In the three-dimensional image projection apparatus according to the invention, the projection unit may project, as the projection image of the three-dimensional image, a projection image of a simulation image for an operation or a projection image of an image including treatment information on the screen.

In the three-dimensional image projection apparatus according to the invention, the projection unit may project vital information on the screen.

According to the invention, there is provided a three-dimensional image projection method comprising: recognizing a position of a screen and a posture of the screen in a three-dimensional space; projecting a projection image of a three-dimensional image of a subject on the screen on the basis of the recognized position of the screen; and changing parameters of three-dimensional image processing performed for the three-dimensional image, on the basis of a change in the recognized posture of the screen in the three-dimensional space or a change in the projection image of the three-dimensional image projected on the screen.

According to the invention, there is provided a three-dimensional image projection control program that causes a computer to function as: a screen recognition unit that recognizes a position of a screen and a posture of the screen in a three-dimensional space; a projection unit control unit that controls a projection unit such that a projection image of a three-dimensional image of a subject is projected on the screen on the basis of the position of the screen recognized by the screen recognition unit; and a three-dimensional image processing unit that changes parameters of three-dimensional image processing performed for the three-dimensional image, on the basis of a change in the posture of the screen in the three-dimensional space, which is recognized by the screen recognition unit, or a change in the projection image of the three-dimensional image projected on the screen.

According to the three-dimensional image projection apparatus, the three-dimensional image projection method, and the three-dimensional image projection control program of the invention, the position of the screen and the posture of the screen in the three-dimensional space are recognized. The projection image of the three-dimensional image of the subject is projected on the screen on the basis of the recognized position of the screen. The parameters of the three-dimensional image processing performed for the three-dimensional image are changed on the basis of a change in the recognized posture of the screen in the three-dimensional space or a change in the projection image of the three-dimensional image projected on the screen. Therefore, it is not necessary for the user to directly touch a three-dimensional image processing apparatus and it is possible to easily change the parameters of three-dimensional image processing without any sanitary problems.

DESCRIPTION OF THE PREFERRED EMBODIMENTS

Figure 1:
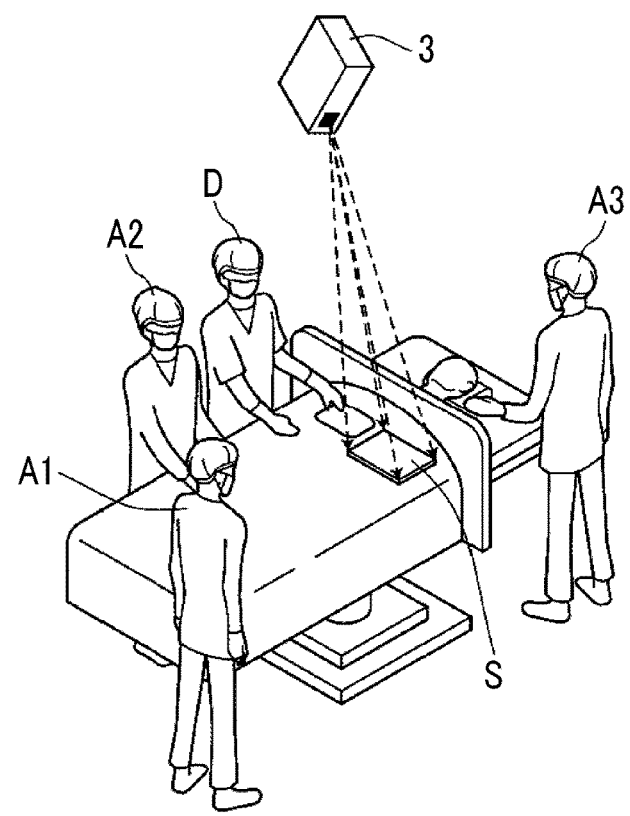
FIG. 1 is a diagram illustrating the usage of a medical image projection system using an embodiment of a three-dimensional image projection apparatus according to the invention.

Hereinafter, a medical image projection system using an embodiment of a three-dimensional image projection apparatus according to the invention will be described with reference to the drawings. FIG. 1 is a diagram illustrating the usage of the medical image projection system according to this embodiment.

Figure 2:
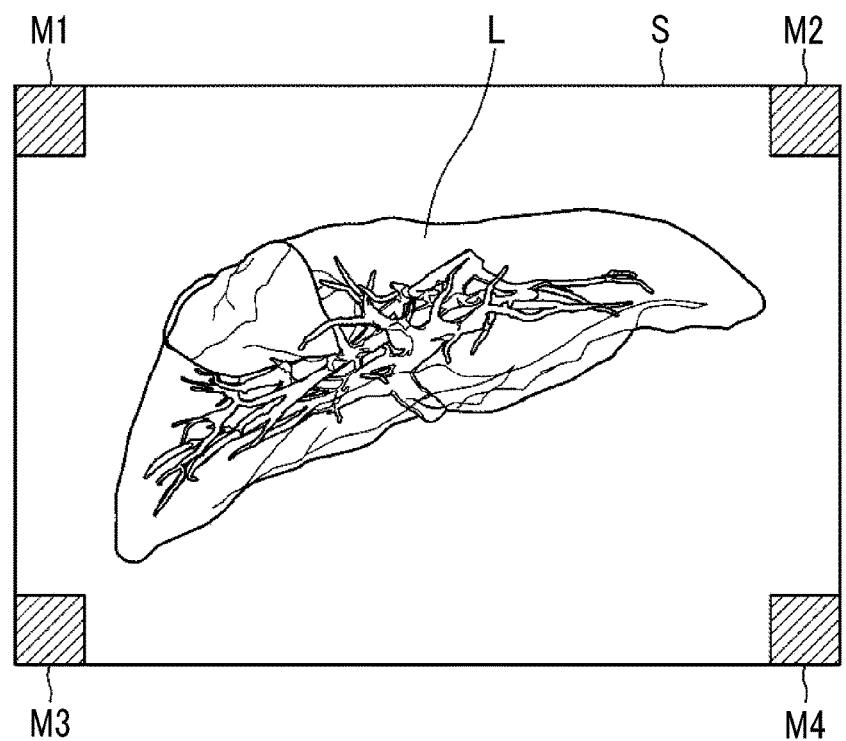
FIG. 2 is a diagram illustrating an example of a projection image projected on a screen.

As illustrated in FIG. 1, in the medical image projection system according to this embodiment, a projector apparatus 3 projects a three-dimensional image of the organs of a patient, who is to be operated on, on a screen S that is provided at any position, for example, in the vicinity of an operative field. For example, the medical image projection system according to this embodiment is used in a situation in which a surgeon D who represents a conference gives various explanations for an operation to participants A1 to A4 before the operation. FIG. 2 is a diagram illustrating an example of the three-dimensional image of the organs displayed on the screen S. For example, as illustrated in FIG. 2, in a case in which the patient is operated on for the liver, a three-dimensional image 6 of the liver L of the patient which has been captured in advance is displayed on the screen S. In addition, markers M1 to M4 provided on the screen S will be described in detail below.

Figure 3:
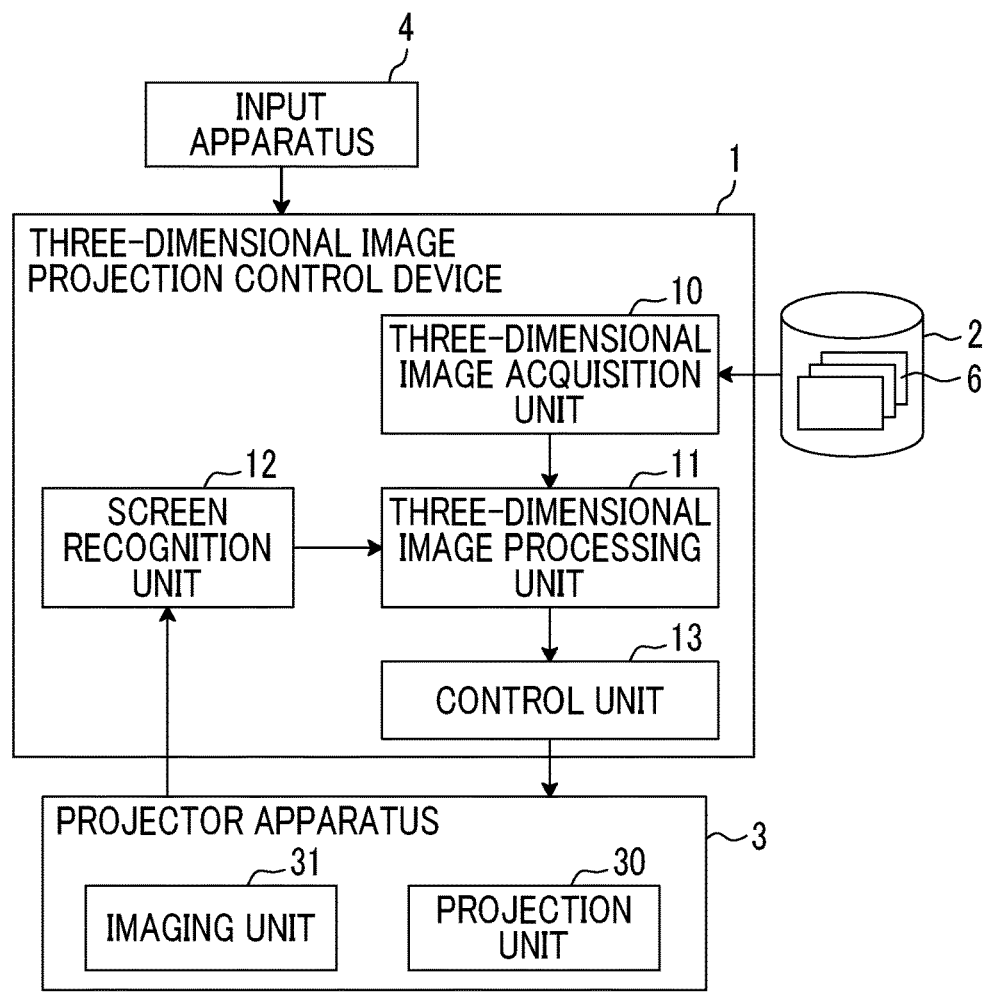
FIG. 3 is a block diagram schematically illustrating the configuration of the medical image projection system.

FIG. 3 is a block diagram schematically illustrating the configuration of the medical image projection system according to this embodiment. Specifically, as illustrated in FIG. 3, the medical image projection system according to this embodiment comprises a three-dimensional image projection control device 1, a medical image storage server 2, the projector apparatus 3, and an input apparatus 4.

The three-dimensional image projection control device 1 is configured by installing a three-dimensional image projection control program according to this embodiment in a computer.

The three-dimensional image projection control device 1 comprises a central processing unit (CPU), a semiconductor memory, and a storage device, such as a hard disk or a solid state drive (SSD). The three-dimensional image projection control program according to this embodiment is installed in the storage device. The three-dimensional image projection control program is executed by the central processing unit such that a three-dimensional image acquisition unit 10, a three-dimensional image processing unit 11, a screen recognition unit 12, and a control unit 13 (corresponding to a projection unit control unit according to the invention) illustrated in FIG. 3 operate.

The three-dimensional image projection control program is recorded on a recording medium, such as a digital versatile disc (DVD) or a compact disc read only memory (CD-ROM), is distributed, and is installed in the computer from the recording medium. Alternatively, the three-dimensional image projection control program is stored in a memory device of a server computer connected to a network or a network storage such that it can be accessed from the outside. Then, the three-dimensional image projection control program is downloaded and installed in response to a request.

The three-dimensional image acquisition unit 10 acquires the three-dimensional image 6 of the patient (subject) which has been captured in advance. For example, the three-dimensional image 6 is generated by performing volume rendering or surface rendering for volume data captured by a computed tomography (CT) apparatus or a magnetic resonance imaging (MM) apparatus. In this embodiment, the case in which the three-dimensional image 6 of the liver of the patient is acquired has been described. However, the invention is not limited thereto. For example, the three-dimensional image of other organs, such as the lungs, the heart, and the head, may be acquired.

The three-dimensional image 6 is stored in the medical image storage server 2 in advance together with identification information of the patient and the three-dimensional image acquisition unit 10 reads the three-dimensional image 6 with the identification information from the medical image storage server 2 on the basis of the identification information of the patient input by the user through, for example, the input apparatus 4 and temporarily stores the three-dimensional image 6.

The three-dimensional image processing unit 11 performs three-dimensional image processing for the three-dimensional image 6 acquired by the three-dimensional image acquisition unit 10. The three-dimensional image processing unit 11 according to this embodiment changes parameters of the three-dimensional image processing to perform the three-dimensional image processing. Specifically, the three-dimensional image processing unit 11 changes parameters of a viewing direction of the three-dimensional image 6 to perform a rotation process, thereby changing the posture of the three-dimensional image 6. In addition, the three-dimensional image processing unit 11 changes parameters of transparency in a case in which volume rendering or surface rendering is performed or performs a highlighting process for a portion of the three-dimensional image 6. The three-dimensional image processing is not limited to these processes and may be other known processes.

First, the three-dimensional image processing unit 11 performs the three-dimensional image processing using parameters which have been initially set. Then, in a case in which the posture of the screen S in a three-dimensional space is changed, the three-dimensional image processing unit 11 changes the parameters of the three-dimensional image processing according to the change. In a case in which an initial projection surface of the screen S on which the three-dimensional image 6 is projected is an initial reference surface, it is assumed that the change in the posture of the screen S in the three-dimensional space includes at least a change in the inclination of the projection surface of the screen S with respect to the initial reference surface.

The screen recognition unit 12 recognizes the position of the screen S which has been randomly provided and the posture of the screen S in the three-dimensional space. The screen recognition unit 12 recognizes the position of the screen S and the posture of the screen S in the three-dimensional space on the basis of the image of the screen S captured by an imaging unit 31, which will be described below, in the projector apparatus 3.

Figure 4:
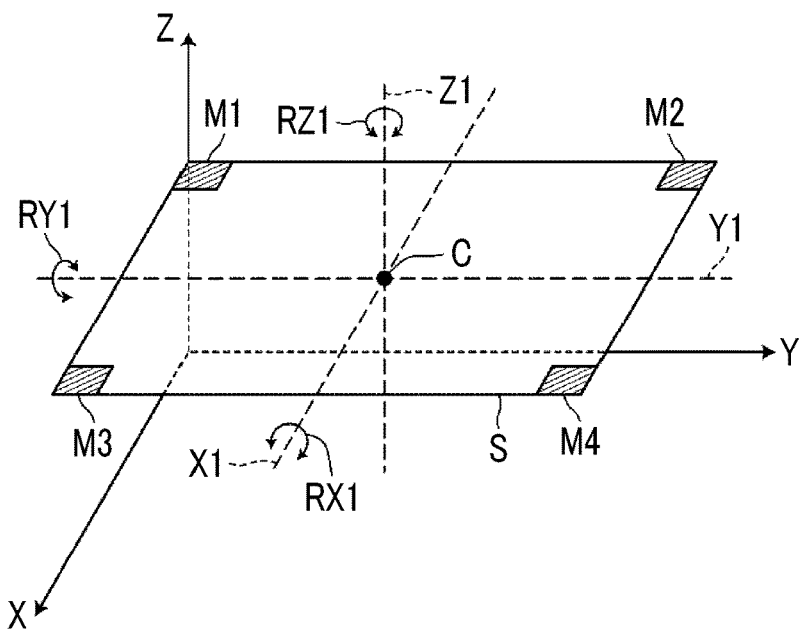
FIG. 4 is a diagram illustrating the configuration of the screen and a change in the posture of the screen.

As illustrated in FIG. 4, the screen S is a flat plate having a rectangular shape and the markers M1 to M4 are provided at four corners of the screen S. The markers M1 to M4 may have a rectangular shape as illustrated in FIG. 4 or may have other shapes including a cross shape.

Then, the screen recognition unit 12 recognizes the position of the screen S and the posture of the screen S in the three-dimensional space on the basis of the arrangement relationship among the four markers M1 to M4 provided on the screen S. Examples of the position of the screen S include a position in the X-Y plane illustrated in FIG. 4 and a position in the Z direction. In this embodiment, it is assumed that the X-Y plane is the horizontal plane and the Z direction is the vertical direction. Further, in this embodiment, it is assumed that the screen S is provided on, for example, the abdomen of the patient who lies on the bed and is substantially horizontally provided at the beginning. However, the initial position and posture of the screen S are not limited thereto and the screen recognition unit 12 recognizes a change from the initial position and posture of the screen S.

Figure 5:
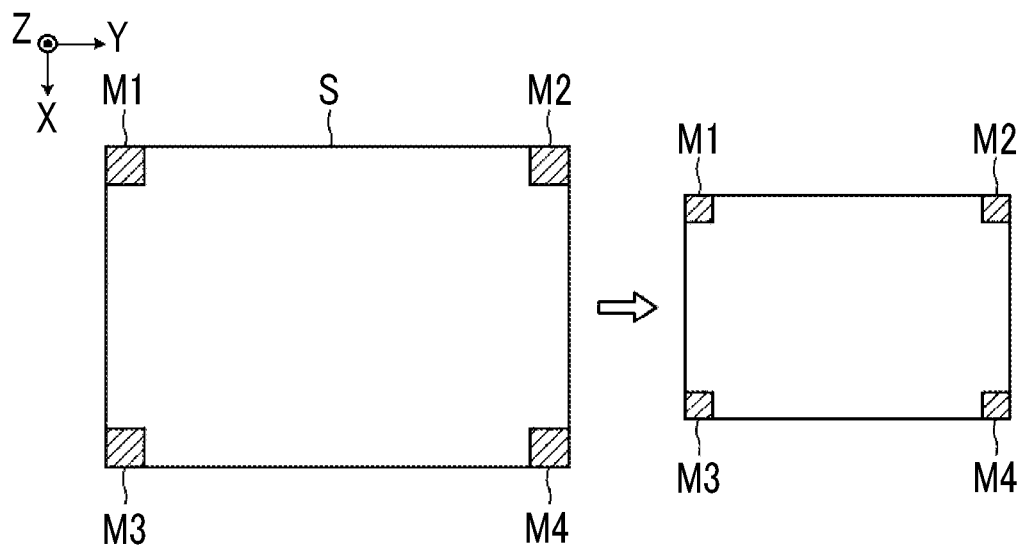
FIG. 5 is a diagram illustrating the recognition of a change in the position of the screen on the basis of markers provided on the screen.

Specifically, in a case in which the four markers M1 to M4 of the screen S are moved in the X-Y plane while maintaining their positional relationship, the screen recognition unit 12 recognizes that the screen S has been moved in parallel in the X-Y plane. In addition, in a case in which the size of a rectangle defined by the four markers M1 to M4 of the screen S decreases or increases while the rectangle is maintained as illustrated in FIG. 5, the screen recognition unit 12 recognizes that the screen S has been moved in the Z direction.

Figure 6:
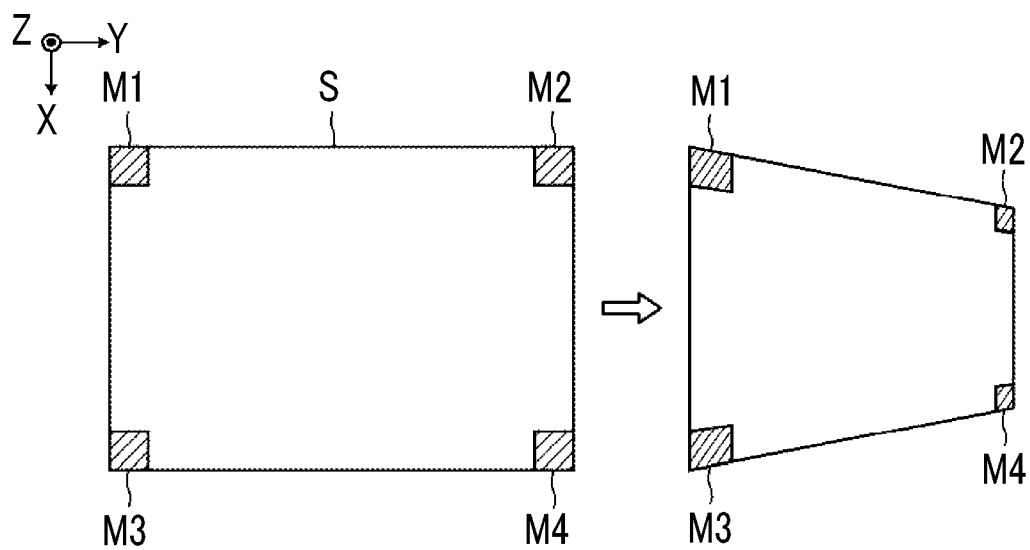
FIG. 6 is a diagram illustrating the recognition of a change in the posture of the screen on the basis of the markers provided on the screen.

In a case in which a distance between the marker M1 and the marker M3 arranged in a line along one end (in FIG. 6, the left end) among the four markers M1 to M4 of the screen S is greater than a distance between the marker M2 and the marker M4 arranged in a line along the other end (in FIG. 6, the right end) while the positional relationship between two markers M1 and M3 is maintained as illustrated in FIG. 6, the screen recognition unit 12 recognizes that the screen S has been rotated. Specifically, the screen recognition unit 12 recognizes that the screen S has been rotated about a straight line X1, which passes through the center C of the screen S illustrated in FIG. 4 and extends in the X direction, as a rotation axis in the direction of an arrow RX1. Similarly, the screen recognition unit 12 recognizes the rotation of the screen S about a straight line Y1, which passes through the center C of the screen S and extends in the Y direction, as a rotation axis in the direction of an arrow RY1, on the basis of the positional relationship among the four markers M1 to M4. In addition, the screen recognition unit 12 recognizes the rotation of the screen S about a straight line Z1, which passes through the center C of the screen S and extends in the Z direction, as a rotation axis in the direction of an arrow RZ1, on the basis of the positional relationship among the four markers M1 to M4.

In this embodiment, the position of the screen S and the posture of the screen S in the three-dimensional space are recognized using the four markers M1 to M4 provided on the screen S. However, the markers may not be necessarily provided. For example, the position of the screen S and the posture of the screen S in the three-dimensional space may be recognized on the basis of the screen S. Specifically, the edge of the screen S may be detected and the position of the screen S and the posture of the screen S in the three-dimensional space may be recognized on the basis of, for example, the position and length of the edge.

In this embodiment, the position of the screen S and the posture of the screen S in the three-dimensional space are detected on the basis of the captured image of the screen S. However, the invention is not limited thereto. For example, the position of the screen S and the posture of the screen S in the three-dimensional space may be detected by other known techniques. Specifically, for example, an acceleration sensor may be provided on the screen S and the position of the screen S and the posture of the screen S in the three-dimensional space may be recognized on the basis of a detection signal of the acceleration sensor.

Figure 7:
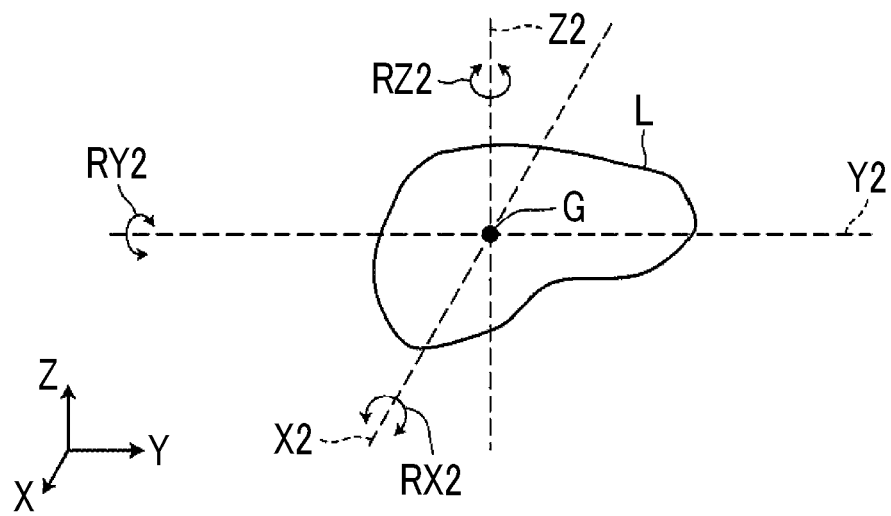
FIG. 7 is a diagram illustrating a process of rotating a three-dimensional image.

As described above, in a case in which the posture of the screen S in the three-dimensional space is changed, the three-dimensional image processing unit 11 according to this embodiment changes the parameters of three-dimensional image processing according to the change. Specifically, for example, in a case in which the screen S is rotated in the direction of the arrow RY1 illustrated in FIG. 4, the three-dimensional image 6 of the liver L currently projected on the screen S is rotated according to the rotation. Specifically, the three-dimensional image 6 of the liver L illustrated in FIG. 7 is rotated in the same rotation direction as the screen S, that is, the direction of an arrow RY2 and by the same rotation angle as the screen S. In addition, it is assumed that the coordinate system of the screen S illustrated in FIG. 4 is matched with the coordinate system of the three-dimensional image 6 of the liver L illustrated in FIG. 7. It is assumed that the center C of the screen S corresponds to the center of gravity G of the three-dimensional image 6 of the liver L and the straight lines X1, Y1, and Z1 illustrated in FIG. 4 correspond to straight lines X2, Y2, and Z3 illustrated in FIG. 7, respectively.

For example, in a case in which the screen S is rotated in the direction of the arrow RX1 illustrated in FIG. 4, the three-dimensional image processing unit 11 rotates the three-dimensional image 6 of the liver L currently projected on the screen S in the direction of the arrow RX2 illustrated in FIG. 7 by the same rotation angle as the screen S.

As such, the three-dimensional image 6 of the liver L is rotated according to the inclination of the projection surface of the screen S to adjust the three-dimensional image projected on the projection surface to a three-dimensional image in the direction desired to be seen by, for example, a doctor. Therefore, tumors under intricate and intertwined blood vessels can be easily seen and it is possible to give a sense of depth to a projection image such that the projection image can be easily seen.

In a case in which the projection surface of the screen S is inclined with respect to the horizontal plane, a so-called trapezoidal process may be performed for the three-dimensional image 6 according to the inclination direction.

For example, in a case in which the screen S is rotated in the direction of the arrow RZ1 illustrated in FIG. 4, the three-dimensional image processing unit 11 rotates the three-dimensional image 6 of the liver L currently projected on the screen S in the direction of the arrow RZ2 illustrated in FIG. 7 by the same rotation angle as the screen S.

Next, returning to FIG. 3, the control unit 13 controls the overall operation of the three-dimensional image projection system. In particular, the control unit 13 according to this embodiment controls the operation of the projector apparatus 3. The projector apparatus 3 comprises a projection unit 30 and the imaging unit 31.

The projection unit 30 projects a projection image of the three-dimensional image 6 acquired by the three-dimensional image acquisition unit 10 on the screen S on the basis of the three-dimensional image 6. The projection unit 30 comprises, for example, a light source, a display panel for displaying the three-dimensional image 6, and a projection lens. In addition, known devices can be used as the projection unit 30.

The projection unit 30 is configured so as to control the projection range of the three-dimensional image 6. The positional information of the screen S recognized by the screen recognition unit 12 in the X-Y plane is output to the control unit 13 and the control unit 13 controls the projection unit 30 on the basis of the positional information of the screen S in the X-Y plane. The projection unit 30 controls the projection range of the three-dimensional image 6 under the control of the control unit 13 and projects the projection image of the three-dimensional image 6 on the screen S.

In a case in which the screen S is moved in the X-Y plane, the screen recognition unit 12 recognizes the position of the moved screen S in the X-Y plane and the control unit 13 controls the projection unit 30 on the basis of the positional information of the moved screen S in the X-Y plane. That is, the projection unit 30 controls the projection range of the three-dimensional image 6 and projects the projection image of the three-dimensional image 6 on the moved screen S. As such, the projection unit 30 sets the projection range of the three-dimensional image 6, following the movement of the screen S. Therefore, for example, even in a case in which a user, such as a doctor, moves the screen S, it is possible to always project the projection image of the three-dimensional image 6 on the screen S.

The imaging unit 31 is a so-called video camera and comprises, for example, an imaging element, such as a charge coupled device (CCD), a lens, and an image processing unit that performs a process for improving the quality of an image captured by the imaging element. The imaging unit 31 captures a video of the operating room in which the screen S is provided. The video captured by the imaging unit 31 is output to the screen recognition unit 12 of the three-dimensional image projection control device 1. The screen recognition unit 12 recognizes the position of the screen S and the posture of the screen S in the three-dimensional space on the basis of each image frame of the input video.

Figure 8:
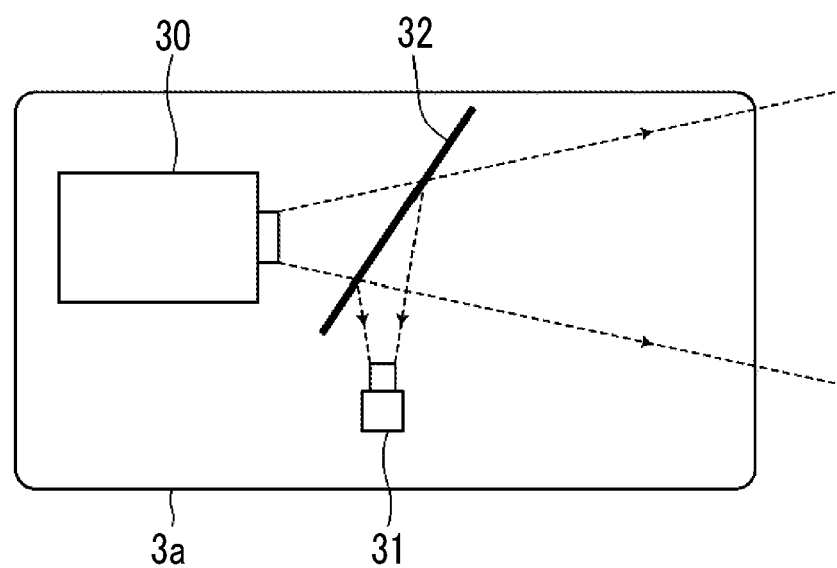
FIG. 8 is a diagram schematically illustrating the configuration of a projector apparatus.

FIG. 8 is a diagram schematically illustrating the configuration of the projector apparatus 3 and is a diagram illustrating the arrangement relationship between the projection unit 30 and the imaging unit 31 in the projector apparatus 3. As illustrated in FIG. 3, in the projector apparatus 3, the projection unit 30, the imaging unit 31, and a beam splitter 32 are provided in a housing 3a. The beam splitter 32 transmits the projection image emitted from the projection unit 30 and reflects the image of the operating room including the screen S to the imaging unit 31.

The projection unit 30 and the imaging unit 31 are arranged in a direction perpendicular to the beam splitter 32. The projection unit 30 and the imaging unit 31 are fixed in the housing 3a in advance in the arrangement relationship in which the optical axis of an optical system of the projection unit 30 is aligned with the optical axis of an optical system of the imaging unit 31 and the angle of view of the projection unit 30 is matched with the angle of view of the imaging unit 31. In this way, the projection range of the projection unit 30 can be substantially equal to the imaging range of the imaging unit 31.

In this embodiment, as described above, the projector apparatus 3 in which the arrangement relationship between the projection unit 30 and the imaging unit 31 is fixed in advance is used. However, the invention is not necessarily limited thereto. The projection unit 30 and the imaging unit 31 may be configured as separate devices.

In this embodiment, as described above, the projection range of the projection unit 30 is substantially equal to the imaging range of the imaging unit 31. However, the invention is not limited thereto. The imaging range of the imaging unit 31 may be wider than the projection range of the projection unit 30. This setting makes it possible to recognize the current projection range. In addition, conversely, in a case in which the imaging range of the imaging unit 31 is narrower than the projection range of the projection unit 30, it is preferable to perform calibration such that the imaging range of the imaging unit 31 is substantially equal to the projection range of the projection unit 30 or is wider than the projection range.

The projector apparatus 3 is installed on, for example, the ceiling or wall of the operating room. However, the position and posture of the projector apparatus 3 may be changed. As the configuration in which the position of the projector apparatus 3 is changed, for example, a rail mechanism that moves the projector apparatus 3 may be provided. In addition, that the posture of the projector apparatus 3 can be changed means that the direction of the optical axes of the projection unit 30 and the imaging unit 31 in the projector apparatus 3 can be changed. A known configuration, such as a configuration in which the housing 3a of the projector apparatus 3 is supported so as to be rotatable, can be used as the configuration in which the posture of the projector apparatus 3 can be changed.

The medical image storage server 2 is a computer that stores and manages various kinds of data and comprises a high-capacity memory device and a database management program. The medical image storage server 2 acquires, for example, the three-dimensional image 6 which has been captured in advance from an imaging apparatus, such as a CT apparatus, through the network, stores the three-dimensional image 6 in the high-capacity memory device, and manages three-dimensional image.

The input apparatus 4 receives the input of various settings by the user and comprises input devices such as a keyboard and a mouse. The input apparatus 4 receives, for example, the input of the setting of the identification information of the patient.

Figure 9:
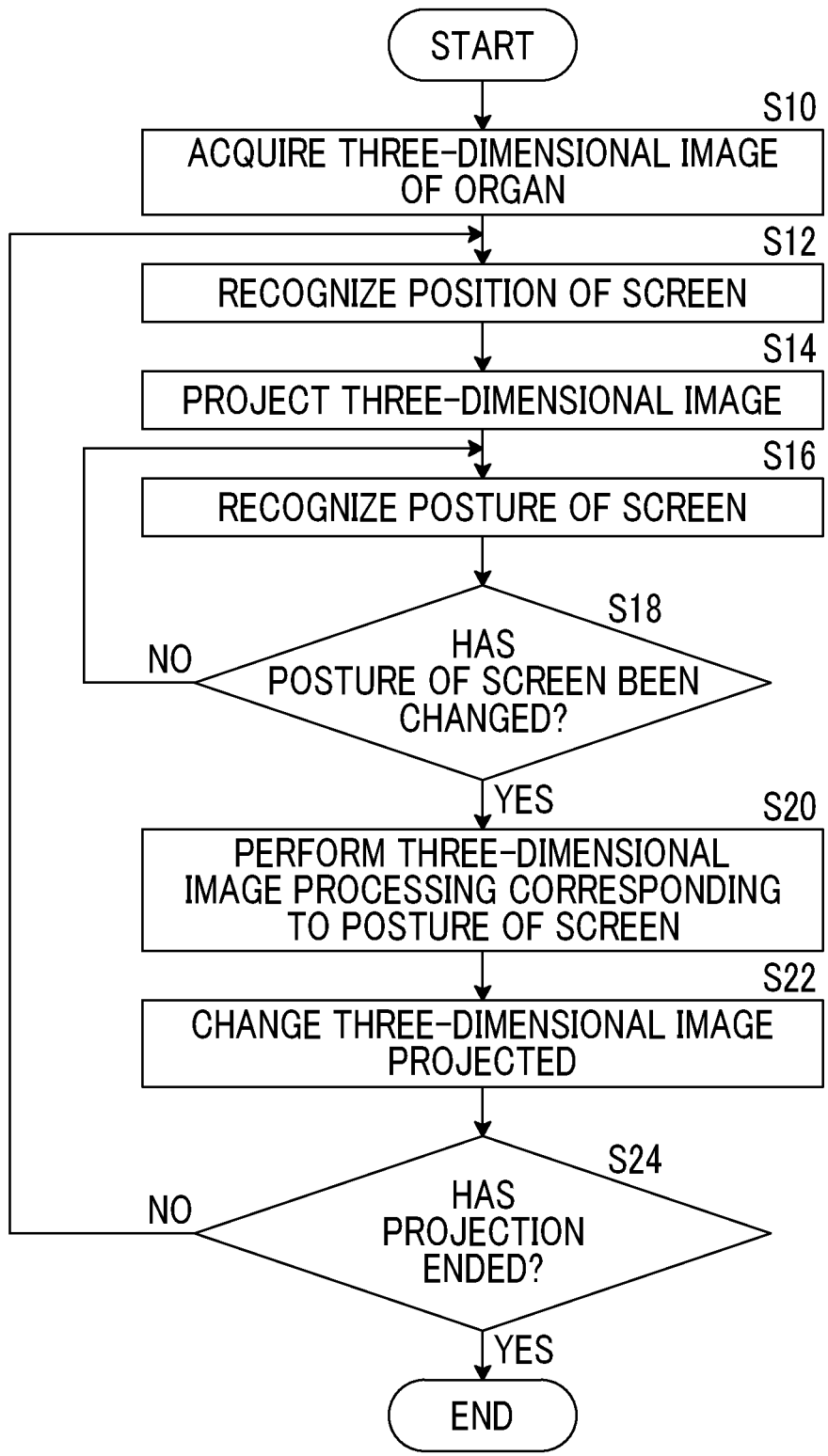
FIG. 9 is a flowchart illustrating the operation of the medical image projection system using an embodiment of the three-dimensional image projection apparatus according to the invention.

Next, the operation of the medical image projection system according to this embodiment will be described with reference to a flowchart illustrated in FIG. 9.

First, the three-dimensional image acquisition unit 10 acquires the three-dimensional image 6 of the organs of the patient in response to the input of settings, such as the identification information of the patient, by the user (S10). In this embodiment, as described above, the three-dimensional image 6 of the liver L is acquired.

Then, the three-dimensional image processing unit 11 performs three-dimensional image processing which has been initially set for the three-dimensional image 6 of the liver L acquired by the three-dimensional image acquisition unit 10 and outputs the three-dimensional image 6 to the control unit 13. In addition, in particular, as the initially set three-dimensional image processing, no processing may be performed.

The imaging unit 31 captures a video of the operating room and the video is input to the screen recognition unit 12. The screen recognition unit 12 recognizes the position of the screen S on the basis of the input video (S12). The positional information of the screen S recognized by the screen recognition unit 12 is output to the control unit 13.

Then, the control unit 13 outputs a control signal to the projection unit 30 of the projector apparatus 3 on the basis of the input positional information of the screen S and the input three-dimensional image of the liver L. The projection unit 30 projects a projection image of the three-dimensional image of the liver L at the position of the screen S provided in the operating room under the control of the control unit 13 (S14).

Then, after the projection of the projection image of the three-dimensional image of the liver L starts, the video captured by the imaging unit 31 is continuously input to the screen recognition unit 12 and the posture of the screen S in the three-dimensional space is recognized (S16).

Then, for example, in a case in which a user, such as a doctor, inclines the projection surface of the screen S with respect to the horizontal plane such that the posture of the screen S in the three-dimensional space is changed (S18, YES), the three-dimensional image processing unit 11 changes the parameters of three-dimensional image processing to perform three-dimensional image processing corresponding to the posture of the screen S for the three-dimensional image 6 of the liver L (S20). Specifically, in this embodiment, a rotation process corresponding to the inclination of the projection surface of the screen S is performed for the three-dimensional image 6 of the liver L.

Then, the three-dimensional image 6 of the liver L subjected to the rotation process is output from the three-dimensional image processing unit 11 to the control unit 13. Then, the projection unit 30 changes the projection image of the three-dimensional image 6 projected on the screen S to a projection image of the three-dimensional image 6 after the rotation process under the control of the control unit 13 (S22). While a change in the posture of the screen S in the three-dimensional space is not recognized in S18 (S18, NO), the projection image of the three-dimensional image 6 of the liver L is continuously projected on the screen S.

Then, it is checked whether the user inputs a command to end the projection by the projection unit 30 through the input apparatus 4. In a case in which the projection end command is not input, the process returns to S12 and the position of the screen S is recognized again. The projection image of the three-dimensional image 6 of the liver L is projected on the position of the screen S. In a case in which the position of the screen S is moved, the projection image is projected on the moved position of the screen S (S14). Then, the process from S16 to S24 is repeatedly performed again and the projection image of the three-dimensional image 6 of the liver L corresponding to the posture of the screen S is projected on the screen S.

Then, in a case in which the user inputs a command to end the projection by the projection unit 30 through the input apparatus 4 (S24, YES), the projection of the projection image on the screen S by the projector apparatus 3 ends.

According to the medical image projection system of the above-described embodiment, the position of the screen S which has been provided randomly and the posture of the screen S in the three-dimensional space are recognized and the projection image of the captured three-dimensional image 6 of the subject is projected on the basis of the recognized position of the screen S. Then, the parameters of the three-dimensional image processing performed for the three-dimensional image 6 are changed on the basis of the recognized posture of the screen S in the three-dimensional space. Therefore, the user does not need to directly touch an apparatus that performs three-dimensional image processing and it is possible to easily change the parameters of the three-dimensional image processing without any sanitary problems.

In the above-described embodiment, the rotation process is performed for the three-dimensional image 6 according to the inclination of the projection surface of the screen S. However, for example, in a case in which the screen S is reversed from an initial state, a process of rotating the three-dimensional image of the liver L 180° may be performed to generate a projection image such that the rear side of the liver L can be observed and the projection image may be projected. As a method for recognizing the reversal of the screen S, for example, different markers may be provided on the front and rear sides of the screen S.

In the above-described embodiment, in a case in which the screen recognition unit 12 is not capable of recognizing the position of the screen S after movement, the control unit 13 may stop the projection of the projection image on the screen S by the projection unit 30. In a case in which the screen recognition unit 12 is not capable of recognizing the position of the screen S, the image of the screen may not be included in the image captured by the imaging unit 31. As such, in a case in which the projection of the projection image on the screen S is stopped, the user can check that the screen S has been moved to the position that is not capable of being recognized.

Figure 10:
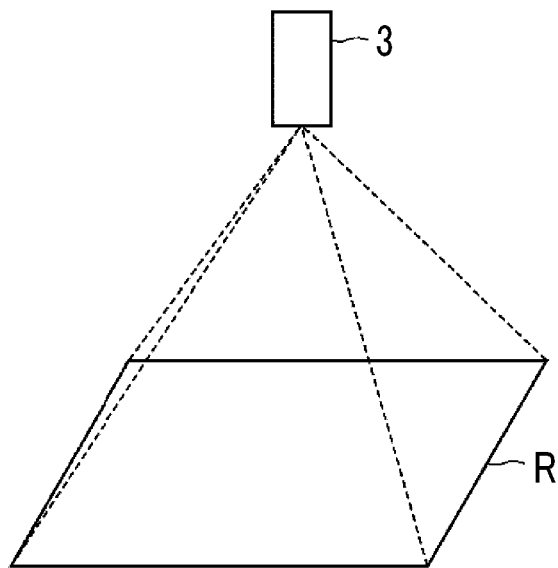
FIG. 10 is a diagram illustrating an example of the projection of an index indicating a projection range of a projection unit.

In the above-described embodiment, the projection unit 30 may project an index indicating a projection range R of the projection unit as illustrated in FIG. 10. The index indicating the projection range R may be, for example, a frame-shaped projection image indicating the projection range R or a projection image indicating only four corners of the projection range R. As such, the projection of the index indicating the projection range R makes it easy for the user to adjust the position of the screen S.

Figure 11:
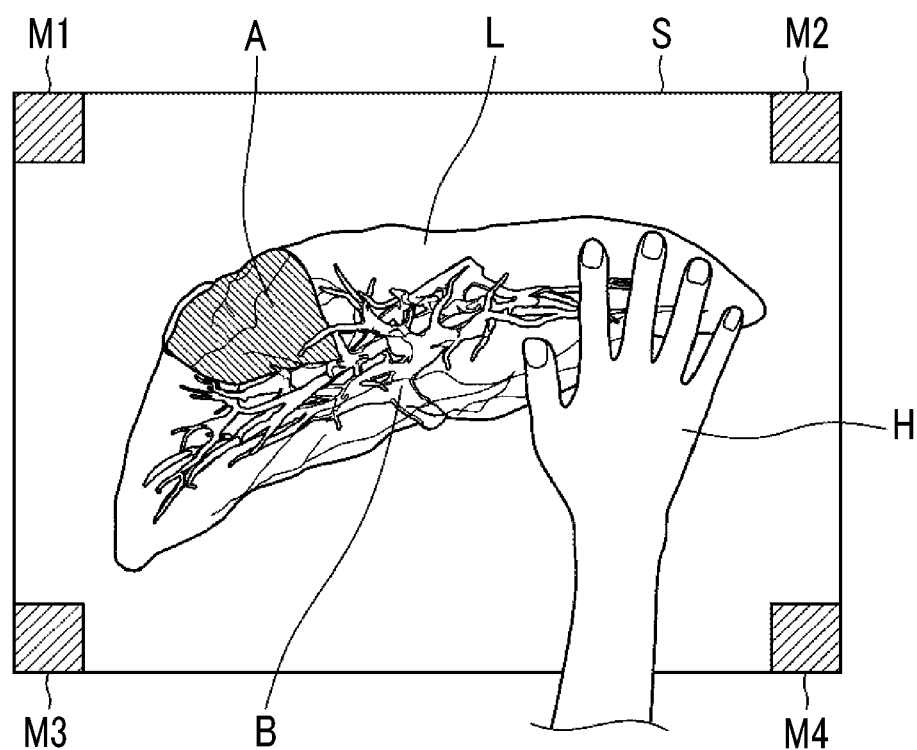
FIG. 11 is a diagram illustrating an example in which a change in a projection image of a three-dimensional image is recognized to change parameters of three-dimensional image processing.

In the above-described embodiment, the posture of the screen S in the three-dimensional space is recognized to change the parameters of three-dimensional image processing. However, the screen recognition unit 12 may recognize a change in the projection image of the three-dimensional image 6 projected on the screen S. In a case in which the screen recognition unit 12 recognizes the change in the projection image of the three-dimensional image, the three-dimensional image processing unit 11 may change the parameters of the three-dimensional image processing. Specifically, for example, in a case in which a hand H of the user touches the three-dimensional image 6 of the liver L as illustrated in FIG. 11, a portion of the projection image of the three-dimensional image 6 of the liver L is missing. The screen recognition unit 12 recognizes the missing of a portion of the projection image and outputs information indicating the missing to the three-dimensional image processing unit 11. Then, the three-dimensional image processing unit 11 changes the parameters of the three-dimensional image processing on the basis of the information. For example, the three-dimensional image processing unit 11 changes the parameters of the three-dimensional image processing to highlight, for example, a blood vessel region B and a dominant region A including a lesion in the three-dimensional image 6 of the liver L. That is, in a case in which the user touches the projection image of the three-dimensional image 6 of the liver L projected on the screen S with the hand H, the blood vessel region B and the dominant region A including the lesion are displayed so as to be highlighted. It is assumed that information of the blood vessel region B and the dominant region A including the lesion is acquired in advance.

In addition, in a case in which the touch of the hand H of the user with the projection image of the three-dimensional image 6 of the liver L is maintained, that is, in a case in which the recognition of the missing of a portion of the projection image continues for a predetermined period of time or more, the transparency of a liver region other than the blood vessel region B and the dominant region A may be changed. That is, the transparency of the liver region may increase such that the user more easily observes the blood vessel region B and the dominant region A. Alternatively, in a case in which the touch of the hand H of the user with the projection image of the three-dimensional image 6 of the liver is maintained after the blood vessel region B and the dominant region A are displayed so as to be highlighted, the liver region other than the blood vessel region B and the dominant region A may not be displayed.

In the above description, the mission of a portion of the projection image is recognized to perform the highlighting process for the three-dimensional image of the liver L or to change transparency. However, the invention is not limited to these types of three-dimensional image processing and other types of three-dimensional image processing may be performed. It is assumed that the type of three-dimensional image processing performed for the three-dimensional image in a case in which the mission of a portion of the projection image is recognized is preset. In addition, for example, a plurality of types of three-dimensional image processing which are performed for the three-dimensional image in a case in which the mission of a portion of the projection image is recognized may be set and the user may select three-dimensional image processing from the plurality of types of three-dimensional image processing. In this case, a selection screen for three-dimensional image processing may be projected on the screen S and the screen recognition unit 12 may recognize that the user touches the selection screen with the hand. In this way, desired three-dimensional image processing is selected.

Figure 12:
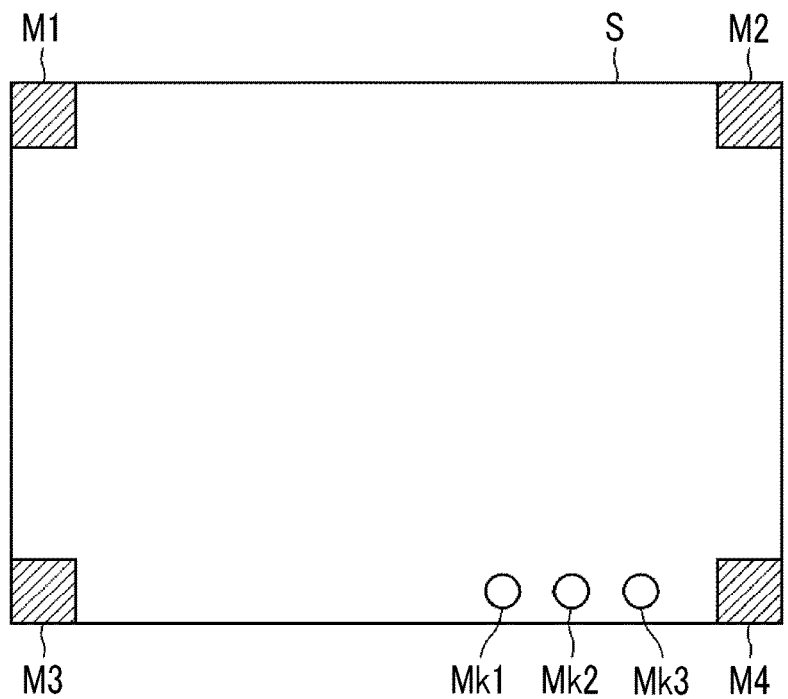
FIG. 12 is a diagram illustrating an example in which a change in a projection image of an operation marker is recognized to change the parameters of the three-dimensional image processing.

In the above description, the touch of the projection image of the three-dimensional image of the liver L by the user is recognized to change the parameters of the three-dimensional image processing. However, the invention is not limited thereto. For example, as illustrated in FIG. 12, projection images of operation markers Mk1 to Mk3 may be projected on the screen S and the screen recognition unit 12 may recognize a change in the projection images of the operation markers Mk1 to Mk3. The three-dimensional image processing unit 11 may change the parameters of the three-dimensional image processing. Specifically, for example, in a case in which the user covers any one of the projection images of the operation markers Mk1 to Mk3 with the hand, the screen recognition unit 12 may recognize that any of the projection images of the operation markers Mk1 to Mk3 disappears and the parameters of the three-dimensional image processing may be changed. For example, the highlighting process may be performed for the blood vessel region B and the dominant region A in a case in which the projection image of the operation marker Mk1 is covered by the user or transparency may be changed in a case in which the projection image of the operation marker Mk2 is covered by the user. In addition, it is assumed that the relationship between the operation marker and three-dimensional image processing performed in a case in which the projection image of the operation marker is covered by the user is preset.

In the above description, in a case in which the user covers a portion of the projection image of the three-dimensional image 6 of the liver L or in a case in which the user covers the projection images of the operation markers Mk1 to Mk3, the highlighting process and the transparency change process are performed. However, the invention is not limited thereto. For example, the highlighting process and the transparency change process may be performed according to the posture of the screen S in the three-dimensional space. That is, in a case in which the user inclines the projection surface of the screen S, the highlighting process or the transparency change process may be performed. In this case, the highlighting process or the transparency change process overlaps the process of rotating the three-dimensional image 6 of the liver L according to the posture of the screen S in the three-dimensional space. The user may select and set the process to be performed in advance. In addition, a selection screen for the process may be projected on the screen S and the screen recognition unit 12 may recognize that the user touches the selection screen with the hand. In this way, desired three-dimensional image processing may be selected.

Figure 13:
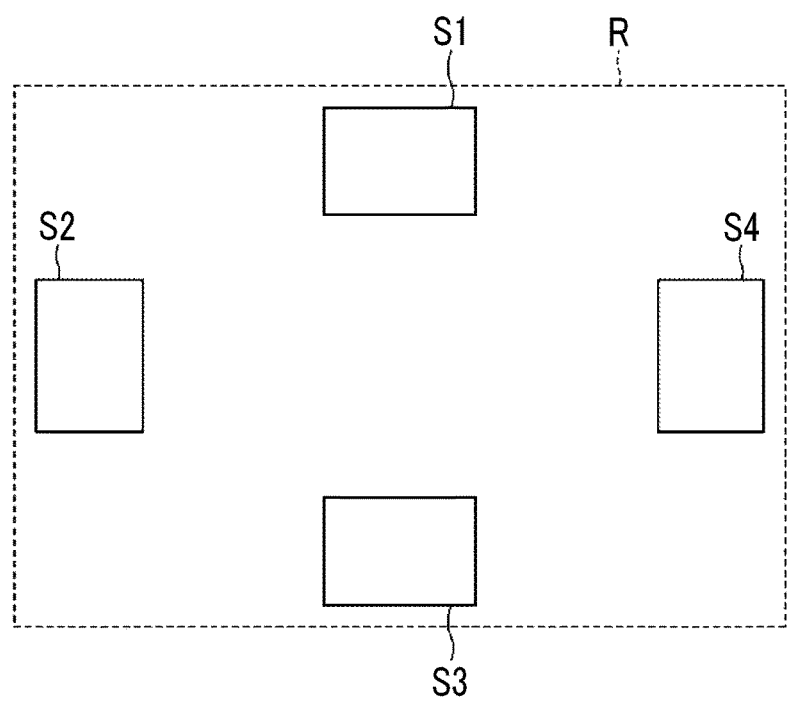
FIG. 13 is a diagram illustrating an example in which projection images are projected on a plurality of screens provided in one projection range.

In the above description, the case in which the projection image of the three-dimensional image 6 is projected on one screen S has been described. However, the invention is not limited thereto. As illustrated in FIG. 13, the projection unit 30 may project the projection images of the three-dimensional images 6 on a plurality of screens S1 to S4 provided in one projection range R. In this case, the projection images projected on the screens S1 to S4 may be the same or may be different from each other. That is, for example, the projection image of the three-dimensional image 6 of the liver L may be projected on each of the screens S1 to S4. Alternatively, the projection image of the three-dimensional image 6 of the liver L may be projected on only the screen S1 observed by the surgeon and projection images different from the projection image of the three-dimensional image 6 of the liver L may be projected on the screens S2 to S4 observed by participants other than the surgeon. Specifically, for example, the vital information of a patient and other kinds of patient information may be projected on the screens S2 to S4 observed by the participants.

In the above-described embodiment, the projection image of the three-dimensional image 6 of the liver L is projected on the screen S. However, a projection image of a simulation image for operation which has been simulated before an operation may be projected on the screen S. For example, a series of images obtained by simulating the procedure of an operation, such as a resection operation, in advance using a three-dimensional image can be used as the simulation image for operation. In addition, a projection image of an image including treatment information may be projected on the screen S. An example of the image including the treatment information is a three-dimensional image 6 including a dose distribution map that shows which part of the body is irradiated with radiation and the amount of radiation emitted to the part in a case in which a radiation treatment is performed before the operation.

In the above-described embodiment, the projection image of the three-dimensional image 6 is projected on the screen S. The projection of the projection image on the screen S and the projection of a projection image on the actual organ of the patient may be switched. Specifically, for example, in a case in which the projection image of the three-dimensional image 6 of the liver L is projected and the user wants to observe the projection image superimposed on the actual liver of the patient, the projection image may be projected on the actual liver of the patient. In a case in which the user wants to observe only the actual liver of the patient, the projection image may be projected on the screen S. In addition, for example, the user may use the input apparatus 4 to switch between the projection of the projection image on the screen S and the projection of the projection image on the actual organ. In addition, in a case in which the projection image is projected on the actual organ, the range of the organ may be recognized on the basis of the image captured by the imaging unit 31 and the projection image may be projected in the range. For the recognition of the range of the organ based on the captured image, for example, the edge of the organ may be detected and other known methods may be used.

EXPLANATION OF REFERENCES

1: three-dimensional image projection control device
2: medical image storage server
3: projector apparatus
3a: housing
4: input apparatus
6: three-dimensional image
10: three-dimensional image acquisition unit
11: three-dimensional image processing unit
12: screen recognition unit
13: control unit
30: projection unit
31: imaging unit
32: beam splitter
C: center of screen
D: surgeon
G: center of gravity of three-dimensional image
H: hand
L: liver
M1 to M4: marker
Mk1 to Mk3: operation marker
R: projection range
S: screen
S1 to S4: screen
X1, X2, Y1, Y2: straight line (rotation axis)
RX1, RX2, RY1, RY2, RZ1, RZ2: rotation direction

What is claimed is:

1. A three-dimensional image projection apparatus comprising:
    a processor configured to
    recognize an inclination of a screen in a three-dimensional space, wherein the screen is a flat plate and configured to be movable three-dimensionally without changing a shape of the flat plate by a user;
    a projection unit that projects a projection image of a three-dimensional image of an organ of a subject on the screen on the basis of the position of the screen; and
    the processor is configured to change parameters of three-dimensional image processing performed for the three-dimensional image, on the basis of a change in the inclination of the screen in the three-dimensional space to perform a rotation process for the projection image of the three-dimensional image projected on the screen.

2. The three-dimensional image projection apparatus according to claim 1,
    wherein the processor is configured to change the parameters of the three-dimensional image processing on the basis of the change in the posture of the screen in the three-dimensional space to change the posture of the projection image of the three-dimensional image.

3. The three-dimensional image projection apparatus according to claim 2,
    wherein the processor is configured to change the parameters of the three-dimensional image processing on the basis of the change in the posture of the screen in the three-dimensional space to perform a rotation process for the three-dimensional image.

4. The three-dimensional image projection apparatus according to claim 3,
    wherein the rotation process is a rotation process using, as a rotation axis, a straight line that extends in a plane of a coordinate system of the three-dimensional image which corresponds to a projection surface of the screen.

5. The three-dimensional image projection apparatus according to claim 1,
    wherein, in a case in which the screen is moved, the processor is configured to recognize a position of the screen after the movement, and
    the projection unit projects the projection image on the screen after the movement.

6. The three-dimensional image projection apparatus according to claim 1,
    wherein the processor is configured to detect a marker provided on the screen to recognize the position of the screen and the posture of the screen in the three-dimensional space.

7. The three-dimensional image projection apparatus according to claim 1,
    wherein the processor is configured to detect the screen to recognize the position of the screen and the posture of the screen in the three-dimensional space.

8. The three-dimensional image projection apparatus according to claim 1,
    wherein the projection unit projects a projection image of an operation marker on the screen,
    the processor is configured to recognize a change in the projection image of the operation marker, and
    the processor is configured to change the parameters of the three-dimensional image processing in a case in which the processor is configured to recognize the change in the projection image of the operation marker.

9. The three-dimensional image projection apparatus according to claim 1,
    wherein the processor is configured to change the parameters of the three-dimensional image processing to change transparency of the three-dimensional image.

10. The three-dimensional image projection apparatus according to claim 1,
    wherein the projection unit projects an index indicating a projection range of the projection unit.

11. The three-dimensional image projection apparatus according to claim 1, further comprising:
    an imaging unit that captures an image of the screen,
    wherein the processor is configured to recognize the position of the screen and the posture of the screen in the three-dimensional space on the basis of the image captured by the imaging unit.

12. The three-dimensional image projection apparatus according to claim 11,
    wherein an arrangement relationship between the projection unit and the imaging unit is fixed in advance.

13. The three-dimensional image projection apparatus according to claim 12, wherein the projection unit and the imaging unit have an arrangement relationship in which optical axes of the projection unit and the imaging unit are aligned with each other and angles of view of the projection unit and the imaging unit are matched with each other.

14. The three-dimensional image projection apparatus according to claim 12,
wherein the imaging unit and the projection unit are configured such that a position or a posture of the imaging unit and the projection unit is changeable.

15. The three-dimensional image projection apparatus according to claim 1,
wherein the projection unit projects the projection images on a plurality of the screens which are provided in one projection range.

16. The three-dimensional image projection apparatus according to claim 15,
wherein the projection unit projects different projection images on the plurality of screens.

17. The three-dimensional image projection apparatus according to claim 1,
wherein the projection unit projects, as the projection image of the three-dimensional image, a projection image of a simulation image for an operation or a projection image of an image including treatment information on the screen.

18. The three-dimensional image projection apparatus according to claim 1,
wherein the projection unit projects vital information on the screen.

19. A three-dimensional image projection method comprising:
recognizing an inclination of a screen in a three-dimensional space, wherein the screen is a flat plate and configured to be movable three-dimensionally without changing a shape of the flat plate by a user;
projecting a projection image of a three-dimensional image of an organ of a subject on the screen on the basis of the position of the screen; and
changing parameters of three-dimensional image processing performed for the three-dimensional image, on the basis of a change in the inclination of the screen in the three-dimensional space to perform a rotation process for the projection image of the three-dimensional image projected on the screen.

20. A non-transitory computer recording medium storing a three-dimensional image projection control program that causes a computer to function as:
a processor configured to
recognize an inclination of a screen in a three-dimensional space, wherein the screen is a flat plate and configured to be movable three-dimensionally without changing a shape of the flat plate by a user;
a projection unit control unit that controls a projection unit such that a projection image of an organ of a three-dimensional image of a subject is projected on the screen on the basis of the position of the screen; and
the processor is configured to change parameters of three-dimensional image processing performed for the three-dimensional image, on the basis of a change in the inclination of the screen in the three-dimensional space to perform a rotation process for the projection image of the three-dimensional image projected on the screen.

21. The three-dimensional image projection apparatus according to claim 1, wherein
the processor is configured to recognize the missing of a portion of the projection image and output information indicating the missing of the portion of the projection image; and
the change in the projection image is indicated by the information indicating the missing of the portion of the projection image.

22. The three-dimensional image projection apparatus according to claim 1, wherein
the missing of a portion of the projection image is caused by a hand of the user.

* * * * *